United States Patent
Trefiak

(10) Patent No.: US 10,114,002 B2
(45) Date of Patent: Oct. 30, 2018

(54) HYDRAULICALLY COUPLED DUAL FLOATING PISTON APPARATUS AND METHODS OF USING SAME FOR SAMPLING HIGH PRESSURE FLUIDS

(71) Applicant: Kurt Trefiak, Edgerton (CA)

(72) Inventor: Kurt Trefiak, Edgerton (CA)

(73) Assignee: Total Analytical Consulting Inc., Edgerton, Alberta (CA)

(*) Notice: Subject to any disclaimer, the term of this patent is extended or adjusted under 35 U.S.C. 154(b) by 191 days.

(21) Appl. No.: 14/978,683

(22) Filed: Dec. 22, 2015

(65) Prior Publication Data

US 2016/0178486 A1    Jun. 23, 2016

Related U.S. Application Data

(60) Provisional application No. 62/095,570, filed on Dec. 22, 2014.

(51) Int. Cl.
*G01N 1/10*    (2006.01)
*G01N 33/28*    (2006.01)

(52) U.S. Cl.
CPC ... *G01N 33/2835* (2013.01); *G01N 2001/105* (2013.01)

(58) Field of Classification Search
CPC ............................ G01N 2001/105; G01N 1/10
See application file for complete search history.

(56) References Cited

U.S. PATENT DOCUMENTS

| | | |
|---|---|---|
| 3,731,530 A * | 5/1973 | Tanguy ............... E21B 21/067 73/152.42 |
| 4,817,445 A * | 4/1989 | Fink ....................... G01N 1/14 73/864.62 |
| 5,303,775 A | 4/1994 | Michaels et al. |
| 5,337,822 A | 8/1994 | Massie et al. |
| 5,609,205 A | 3/1997 | Massie et al. |
| 6,182,757 B1 | 2/2001 | Schultz |
| 6,467,544 B1 | 10/2002 | Brown et al. |
| 6,659,177 B2 | 12/2003 | Bolze et al. |
| 6,668,924 B2 | 12/2003 | Bolze et al. |
| 6,688,390 B2 | 2/2004 | Bolze et al. |
| 7,464,755 B2 | 12/2008 | Edwards |
| 2015/0198039 A1 * | 7/2015 | Marshall ............... E21B 49/086 73/152.42 |

FOREIGN PATENT DOCUMENTS

FR        2792071    * 10/2000

* cited by examiner

*Primary Examiner* — Robert R Raevis
(74) *Attorney, Agent, or Firm* — Ulmer & Berne LLP

(57) ABSTRACT

Apparatuses, methods and uses thereof, for sampling fluids and volatile components in such fluids, from a high pressure pipe, are provided. The apparatus can include dual floating pistons moveably disposed in two cylinders. The lower portion of the first cylinder can be fluidly connected to the upper portion of the second cylinder. In operation, fluids can enter the upper portion of the first cylinder, controlled by flow limiting means. Once the first cylinder is filled with sample, the pressure on the sample can equalize to the pressure set in the lower portion of the second cylinder. The sample can be exposed to gas to liberate the volatile components of the sample into a vapor phase. The sample, or vapor phase, can then be discharged from the first cylinder to an analyzing device. The apparatus, method and use of the present disclosure can reduce the risk of plugging of the system.

13 Claims, 3 Drawing Sheets

HYDRAULICALLY COUPLED DUAL FLOATING PISTON APPARATUS AND METHODS OF USING SAME FOR SAMPLING HIGH PRESSURE FLUIDS

REFERENCE TO RELATED APPLICATION

This application claims priority of U.S. provisional patent application Ser. No. 62/095,570, filed Dec. 22, 2014, and hereby incorporates this provisional patent application by reference herein in its entirety.

TECHNICAL FIELD

The present disclosure relates to sampling high pressure fluids, and more particularly, apparatuses and methods for sampling high pressure fluids.

BACKGROUND

Fluids in the oil and gas industry, such as crude oil or natural gas liquids (NGLs), are shipped under high pressure through lengths of pipe in remote areas. These fluids, also known as dirty hydrocarbons, are regularly analyzed by on-line analyzers as they pass through the pipes. The results are used to optimize blending stations and to ensure tariff limits are not exceeded at receipt points and at major rail car terminals.

A sample of fluid from a high pressure pipe needs to be conditioned before being analyzed by an on-line analyzer. Sample conditioning systems present some challenging design requirements. The process or pipe carrying the fluid of interest can vary widely in terms of pressure, temperature, composition, quality and contamination of the fluid. However, the on-line analyzing device is making sensitive measurements of the variable of interest, and requires that all other variables be tightly controlled. Sample conditioning typically requires pressure reduction, temperature alteration, flow control and implementation of safety mechanisms to ensure the measurement device is not damaged and personnel are not injured.

Conventional on-line analyzer sampling systems are designed for a continuous flow of fluids through filters and the analyzer. These include analyzers for pH, oxygen reduction potential, and dissolved oxygen. However, newer analyzing devices, such as Gas Chromatographs and Vapor Pressure Analyzers, are cyclic analyzers that only grab samples for very short periods of time and require that no fresh sample be taken for comparably long periods of time.

As mentioned above, sampling systems require sample conditioning before measurement, such as cooling, heating, and/or dilution. Because of these sample modifications, the benefits of cycling analyzers can outweigh any drawbacks of discretely sampling of fluids, rather than using continuous or live measurement. Further, in some processes, speed of response may be considered a lower priority than reliability and quality of the results.

Further, when an on-line analyzer fails, is inoperable, or requires maintenance, the pipeline system experiences downtime, which costs the user time and money. Daily maintenance is also exceedingly difficult because of the remote location of these on-line analyzers.

The majority of the system downtime is related to the sample conditioning portion of the on-line analyzer. It is generally known that 80% of all analyzer failures can be attributed to the sample conditioning system, and when dealing with dirty hydrocarbons this percentage can be even higher.

Because the pipe pressure is in significant excess of the on-line analyzer's pressure capabilities in many applications, the first element of conditioning the sample is typically pressure reduction. This can be achieved through the installation of an adequately specified pressure regulator to solve the pressure reduction requirement. Unfortunately, restrictive orifices of any kind, like regulators or needle valves, will plug in a short amount of time in crude oil applications immediately downstream from the restriction leading to failure or inoperability of the sample system.

The high rate of plugging at flow restriction points is due to certain components within crude oil, such as asphaltenes and paraffins (wax), which have a high tendency to precipitate where the flow regime is substantially altered. This includes restrictive elements of the sampling system that affect the flow of the sample. Therefore, pressure regulators, flow control valves, orifices, variable area flowmeters and filters all result in precipitation of these components and a build-up of deposits.

As the deposits at flow restriction points increase, they become so persistent that they can plug flowing systems completely, necessitating cleaning by manual, mechanical, or chemical means. Plugging of this nature has been found to occur in traditional systems in as little as a few minutes in extreme cases, but is commonly on the order of 2 hours to 3 days.

If the plug occurs in a filter assembly, it is an inconvenience because it results in downtime and lost revenue, and loss of the benefit from the measuring device. But, clearance of a filter is a relatively straight forward operation for the technician because the filter is typically selected with a design that is easily maintained. However, should the plug occur in the regulator or flow control device, it becomes a much more arduous task to clear as these devices are not designed to be easily serviced or disassembled. Often they require specialty tools, non-reusable gaskets, seals, o-rings and diaphragms that can be easily damaged and are not intended for regular re-building. Threads gall and/or sealing faces may become scratched and hidden flow passages are small and difficult to mechanically clear.

To date, all traditional methods employed for pressure reduction involve using a small orifice, like a needle valve, regulator or capillary to reduce the pressure. These all tend to plug because of the pressure drop or increased turbulence at the orifice, which causes the waxes and asphaltenes to precipitate and, in turn, eventually plug the sample flow.

Known methods of addressing some of these problems include an automatic backflush system to clear filters, but this only addresses the filter assembly and not the pressure regulation system. Some in the industry have suggested operating certain analyzers at a higher temperature to reduce wax build-up and then correlate the result back to the ASTM International method at 40° C. However, high temperature would reduce the wax precipitate build-up on the sensor, but does not address other sample conditioning challenges.

Hydrogen sulfide ($H_2S$) is a lethal gas and human exposure can lead to serious consequences. It can be found in crude oil and other liquid hydrocarbons and is especially dangerous where personnel expect the fluid to be non-hazardous and free of $H_2S$. Many applications require the concentration of sulfur, typically from $H_2S$, to be below 1 or 2 ppm to be considered "sweet" and acceptable for shipping by rail car, truck or to be processed in many facilities.

Currently, there is no device that is able to provide reliable measurement of $H_2S$ in crude oil and liquid hydrocarbon streams.

Accordingly, there is a need and desire to provide an apparatus and method that can ameliorate or overcome the shortcomings of the prior art.

SUMMARY

An apparatus for sampling dirty hydrocarbon fluids from a high pressure pipe is provided, including a method and use of said apparatus. The present disclosure can address a need in the industry of having a way of sampling fluids from a high pressure pipeline without plugging the flow stream of a sampling device with deposits, like asphatene and/or paraffin.

Broadly stated, in some embodiments, the apparatus can utilize at least two hydraulically coupled pistons to regulate the pressure of a fluid (e.g., dirty and historically troublesome hydrocarbons) to be sampled for on-line analysis. Pressure regulation in this way can decrease the likelihood that the device will become plugged. The process can discretely sample high pressure fluid passing through the pipe, rather than continuously, as is traditional in the industry, although unnecessary.

In some embodiments, the device can be comprised of two cylinders. Each cylinder can be separated into an upper portion and a lower portion by a piston that can be positioned movably in the cylinder. The two pistons can be hydraulically coupled to each other through a fluid connection between the lower part of the first cylinder and the upper part of the second cylinder. A flow limiting means within the fluid connection can regulate the flow rate of the fluid sample into the first cylinder. Either a self-regulating or electronically controlled valve can be functionally connected to the lower portion of the second cylinder.

In operation, in some embodiments, the fluid to be sampled can pass from the high pressure pipe into the upper portion first cylinder through a inlet valve. The flow limiting means in the fluid connection between the first and second cylinders can limit the rate at which the sample enters the first cylinder. Thus, during sampling the pistons can travel in a controlled and repeatable manner.

In some embodiments, at the point that the first cylinder is filled with sample, the inlet valve can be closed and the pressure of the sample in the upper portion of the first cylinder can equalize with the air or hydraulic pressure set for the lower portion of the second cylinder. Pressure regulation can be achieved without the use of any restrictions within the fluid process sample. In some embodiments, a restriction can be in the clean intermediary/hydraulic fluid that joins the first and second cylinders.

In some embodiments, the outlet valve on the first cylinder can then be opened and the self-regulator or electronic regulator valve can increase the pressure in the lower portion of the second cylinder resulting in the sample to be analyzed flowing out of the upper portion of the first cylinder.

In some embodiments, the sample fluid can be unrestricted. Filtration may be required when there is no alternative to removing particulate (crude in particular) other than to have passages small enough to catch the contaminants within the filter element.

In some embodiments, a shaft can be present, which extends through the top of the first cylinder. The shaft can include a gas supply valve, an actuator, a foot valve and either an internal passage or external valve. There may be an inner seal between the hole in the top of the first cylinder and the shaft to prevent the escape of fluid and/or vapour from the upper portion of the first cylinder.

In this embodiment, when the actuator is engaged the foot valve at the bottom of the shaft opens to allow gas to flow into the upper portion of the first cylinder, which contains the liquid hydrocarbon sample to be tested. The flow of gas pushes the first piston downwards until the internal passage is below the top of the first cylinder. Vapour, containing the injected gas and volatile components from the liquid hydrocarbon sample (also referred to as the analyte), is released from the upper portion of the first cylinder through the internal passage and to the analyzer for analysis. Once the analysis is completed, or alternatively no analyte remains in the vapour, the gas supply valve can close and the remaining liquid and vapour can be evacuated from the upper portion of the first cylinder, for example through the sample drain valve.

DETAILED DESCRIPTION OF EMBODIMENTS

Figure 1:
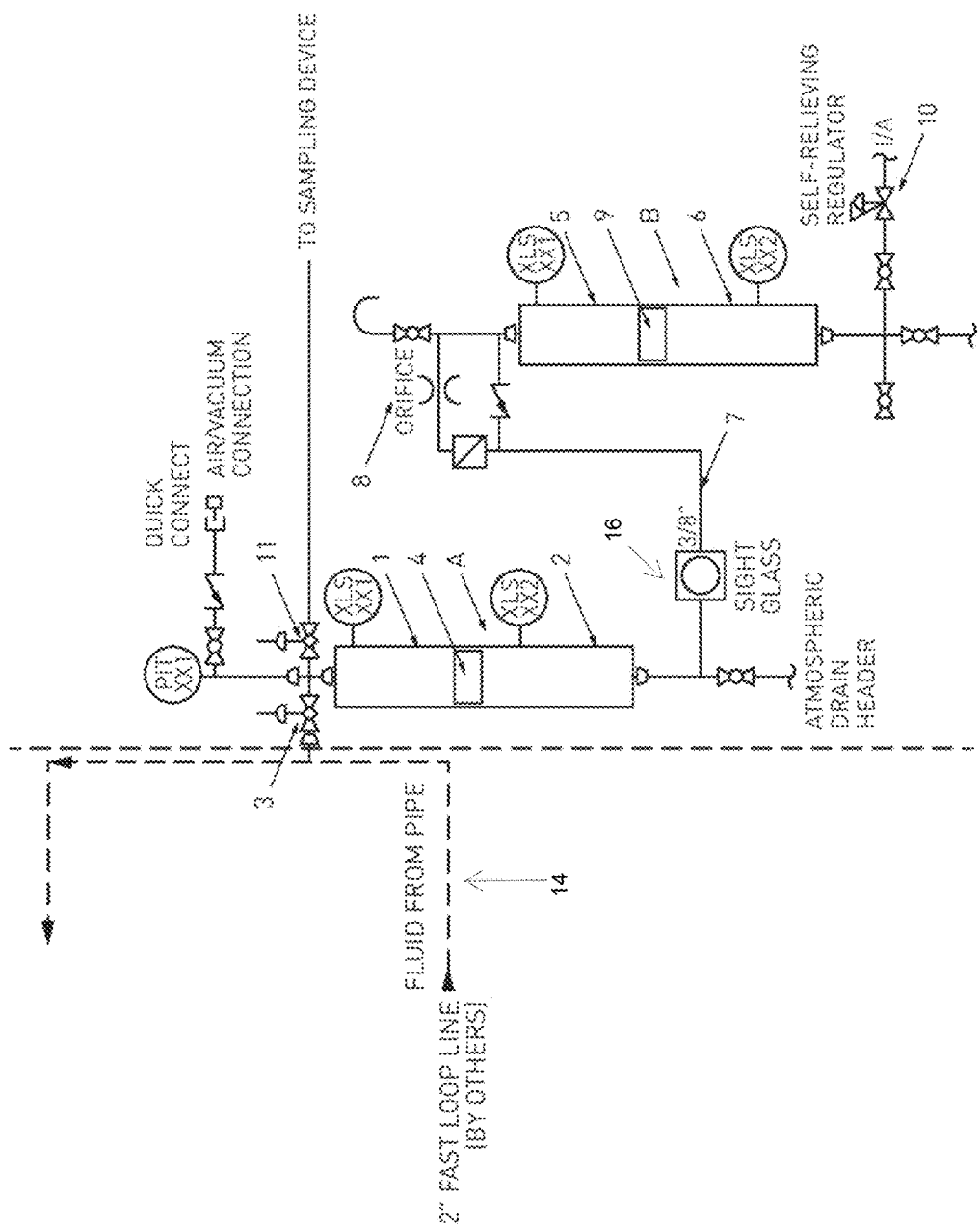
FIG. 1 is a cross-sectional side view of an embodiment of an apparatus used to sample dirty hydrocarbons from a high pressure pipe according to the present disclosure.

Apparatuses, and methods and uses thereof are provided for sampling dirty hydrocarbons from a high pressure pipe. Referring to FIG. 1, broadly stated, in some embodiments, the device can comprise two cylinders A and B. First piston 4 is moveably disposed in cylinder A and piston 9 is movably disposed in cylinder B.

In some embodiments, an inlet valve 3 can be opened to allow sample fluid from the high pressure pipe into the upper portion 1 of the first cylinder A. The lower portion 2 of the first cylinder A can be filled with hydraulic fluid, and can be separated from the sample fluid by a first piston 4. When the upper portion of the first cylinder 1 is filled with sample fluid to a certain set point, for example 80% full, a programmable logic controller (PLC) can be triggered to close the inlet valve 3. In some embodiments, the PLC can be triggered by magnetic means. For example, there can be a magnet located in the first piston 4 that can trigger a magnetic limit switch through the non-ferrous cylinder wall (e.g., constructed of 316SS) so that the system controller can recognize and then close inlet valve 3.

In some embodiments, the length of pistons 4 and 9 can be relatively long in proportion to their diameter. If the length of pistons 4 and 9 is twice their diameter, this can prevent twisting of the piston within the bore of cylinders A and B such that the pistons begin to bind due to metal to metal contact (a phenomenon known as "side loading"). Further, in some embodiments, pistons 4 and 9 can have soft metal wear rings incorporated near the extremities of the pistons to prevent permanent damage to cylinder A and B such as scratches.

In some embodiments, a connecting means 7 can fluidly connect the lower portion 2 of the first cylinder A with the upper portion 5 of the second cylinder B, which together may be referred to as the "intermediate stage". The intermediary fluid, also referred to as hydraulic fluid, can be a hydrocarbon based transmission-hydraulic-gear fluid but may be any other liquid that is compatible with the application and service.

The intermediary/hydraulic fluid within the connecting means 7 can be viewed using, in some embodiments, a sight glass 16, to determine the level of contamination and whether or not the intermediary/hydraulic fluid needs to be replaced. If the hydraulic fluid is nearly clear, then the fluid is uncontaminated. As the apparatus operates the fluid will slowly darken and eventually turn the color of the sample fluid (in the case of crude oil, this would be black). This darkening can be used as an indication of when the intermediary fluid should be changed with fresh fluid.

In some embodiments, a flow limiting means 8 can be positioned within the connecting means 7 to regulate the flow of the hydraulic fluid from the first cylinder A to the second cylinder B, and thereby also regulate the fill rate critical velocity of the upper portion 1 of the first cylinder A. In some embodiments, this flow limiting means can be an orifice or frit.

In some embodiments, the lower portion 6 of the second cylinder B can be filled with gas or fluid. The movement of gas or fluid from the lower portion 6 of the second cylinder B can be regulated by a pressure regulator 10, which may be a self-relieving pressure regulator or, alternatively, a hydraulic pump, an electronically controlled pressure regulating valve, or equivalent means.

Once the inlet valve 3 is closed, the pressure within the device is equalized by the pressure regulator 10 to a particular set point (for example 50 psi). The use of the intermediary fluid can improve the operational reliability of the system by double isolation of the aggressive crude from the sensitive pressure regulator 10.

In some embodiments, the temperature of the sample fluid can be increased or decreased after the pressure in the apparatus has been equalized. By directly heating or cooling the first cylinder A, the fluid sample contained within it can be quickly brought to a stable temperature by electrical means or by low volumes of a heat exchange medium, while maintaining the phase of the fluid. This can involve considerably less cost than a full control system that modulates the flow of a heating medium, such as steam or glycol, through a heat exchanger, not to mention the cost to the associated piping, pumps, exchanger, control valves and instrumentation. Alternatively, where the temperature of the sample fluid needs to be cooled, such as with boiler feed water or similar application, and there is limited or no cooling medium available, the fluid sample can be either passively cooled by ambient air or actively cooled with, for example, Peltier elements, vortex coolers, refrigeration units or other cooling methods. Heating or cooling the fluid sample is generally not possible when using traditional, continuously flowing sample systems, which can have sample fluid moving at variable flow rates.

In some embodiments, the dilution of the sample fluid can be precisely controlled for extremely viscous or dangerous or toxic fluids in other analytical applications after equalization occurs, but before the sample fluid is sent to the analyzer.

In some embodiments, once the second piston 9 reaches a set point, or moves past a limit switch, a PLC within the second cylinder can be triggered to open the outlet valve 11 and the pressure regulator 10 can increase the pressure in the lower portion 6 of the second cylinder B, ultimately resulting in the sample fluid being pushed out of the upper portion 1 of the first cylinder A, through the outlet valve 11 towards the analyzing device.

In some embodiments, once the first piston 4 reaches a set-point within the first cylinder A, the outlet valve 11 can close and the inlet valve 3 can open to allow in a new fluid sample.

In some embodiments, the flow limiting means 8 can be unidirectional or, in other embodiments, it could be bypassed in the reverse direction. For example, the connecting means 7 can include a check-valve to allow an increased flow of hydraulic fluid when the sample fluid is being pushed out of the outlet valve 11. This can allow piston 4 to travel as quickly as required to maintain the required pressure on the sample. In some embodiments, a flow restriction in the analyzer or downstream from the analyzer (such as a capillary) can be used to limit the rate of flow out of the upper portion 1 of the first cylinder A and allow the pistons 4 and 9 to maintain a specified pressure.

In some embodiments, first and second cylinders A and B can be different sizes. For example, the second cylinder B can have a larger diameter than the first cylinder A, and therefore piston 9 would be larger than first piston 4. In such embodiments, the sample fluid can be drawn into the first cylinder A at a certain pressure (for example 100 psi) and pushed out of the first cylinder A at a greater pressure (for example 500 psi).

Industrial process fluids can typically contain some level of solids contamination and crude can have an especially significant amount of sediment, including sand. These solids need to be removed prior to entering the apparatus or there is a risk of reduced service life of the seal on the first piston 4. In some embodiments, a filter system can be used and can include a simple stainless steel screen element as a depth-type filter, designed and configured with the expectation that it will plug. If the filter system is present, certain embodiments can allow a controller to automatically backwash the filter with solvent returning it to new unplugged condition.

Figure 2:
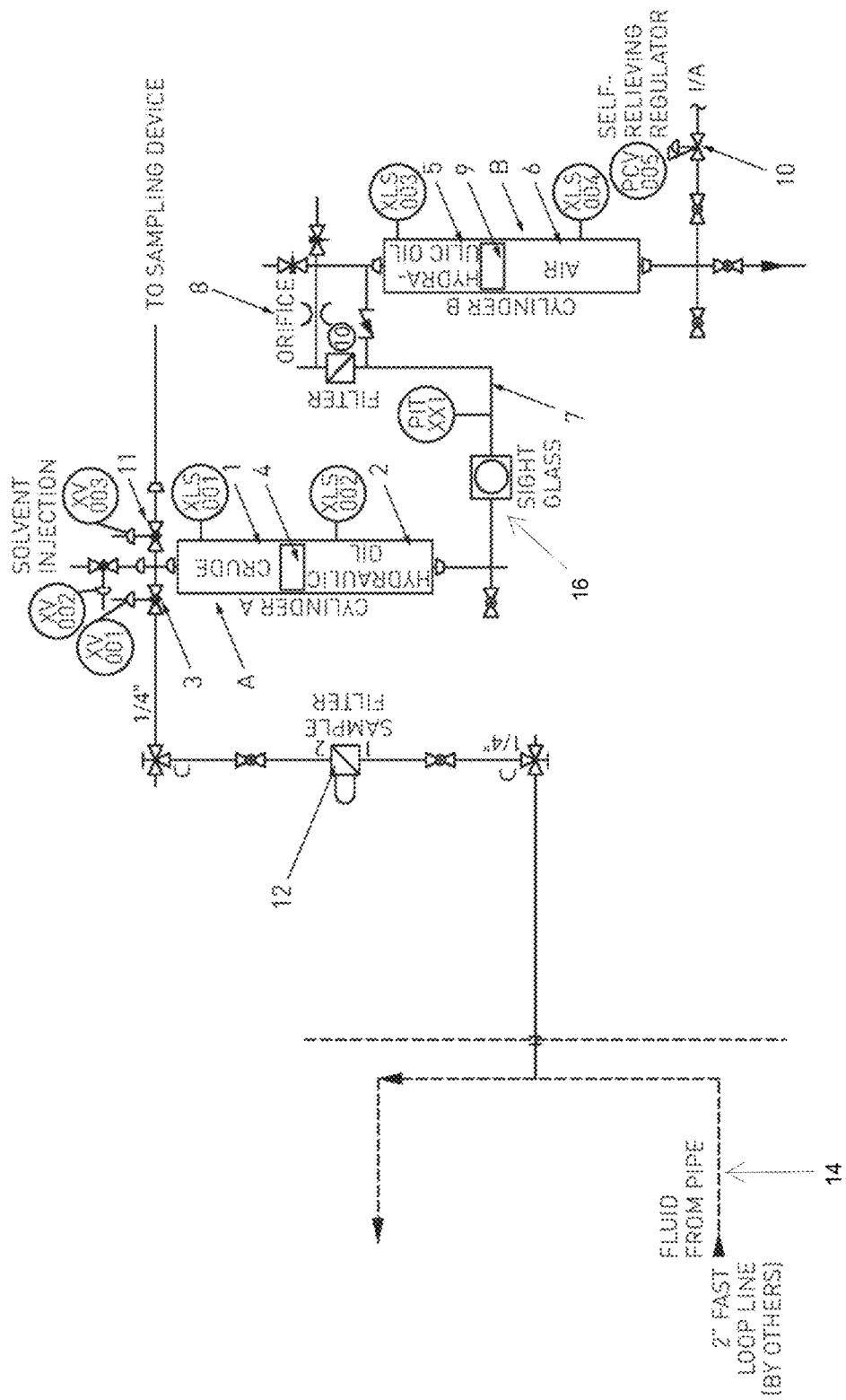
FIG. 2 is a cross-sectional side view of a further embodiment of a device used to sample dirty hydrocarbons from a high pressure pipe according to the present disclosure.

Referring to FIG. 2, in an alternative embodiment, a sample filter 12 can be positioned upstream (e.g. between the high pressure pipe 14 and the inlet valve 3 of the first cylinder A) of the dual piston apparatus and piston 4 or 9 can be configured to push solvent through the filter to clean it. The first piston 4 can be used to draw a solvent from a separate containment vessel and use it to clean the entire flow path through the analyzer or to backwash the filter 12 with a series of valves or to re-inject the accumulated fluid sample into the pressurized pipeline. In some embodiments, a filter pump can be positioned downstream of the dual piston apparatus and a chemical pump can be used to backwash solvent through the filter to clean it.

In some embodiments, redundant filters can be included. For example, the redundant filters can allow for a user to switch between two filters to allow for the uninterrupted operation of the analyzer, even during filter inspection or change out.

Broadly stated, in some embodiments, as the sample fluid is drawn into the upper portion 1 of the first cylinder A by the opening of the inlet valve 3, the pressure in the pipe can overcome the pneumatic actuating pressure (or hydraulic pressure) in the lower portion 6 of the second cylinder B. There can be bleeding back through a pressure regulator 10 as the pistons 4 and 9 retract. The rate at which the pistons retract may be less controlled by the pressure in the lower portion 6 of the second cylinder B than by the flow limiting means 8 in the connecting means 7.

In some embodiments, this controlled rate of travel can ensure that the pressure in the upper portion 1 of the first cylinder A when the inlet valve 3 is opened is at or very near the operating pressure of the pipe thereby eliminating any deposition of asphaltenes. As well, restricting the hydraulic flow rate can allow for a controlled rate of fill to occur, thereby eliminating the potential of slamming the piston into the ends of the cylinder.

In some embodiments, the floating piston design can be tolerant of piston seal damage because the pressures on each side of piston 4 and 9 can be balanced fairly evenly. The only pressure differences required during operation across the pistons 4 and 9 are those needed to move the pistons, which is quite low. In other words, generally, the differential pressure across the pistons is low and, therefore, even with considerable damage to the seals positioned and designed to isolate the upper and lower portions of the cylinders, the volume of sample and intermediary fluid mixing across the seals should remain fairly low for a lengthy period of time.

In some embodiments, once inlet valve 3 is closed, pressure in the upper portion 1 of the first cylinder A can quickly equalize with the pressure in the lower portion 6 of the second cylinder B, since the sample fluid is liquid in nature and typically non-expansible. The first and second pistons 4 and 9 can now be generally stationary except for some small movement attributed to potential thermal expansion effects due to changing ambient conditions or the intentional heating or cooling elements attached to cylinder A. The equalized pressure can remain at the set point of the lower portion 6 of the second cylinder B.

In some embodiments, when the analyzer is ready to analyze the sample fluid, the outlet valve 11 can be opened by a controller signal and the pressure regulator 10 can push the first and second pistons 4 and 9 ahead, ejecting the fluid sample out of the first cylinder A at a precise pressure set at the lower portion 6 of the second cylinder B, which is within the limits of the analyzer.

Figure 3:
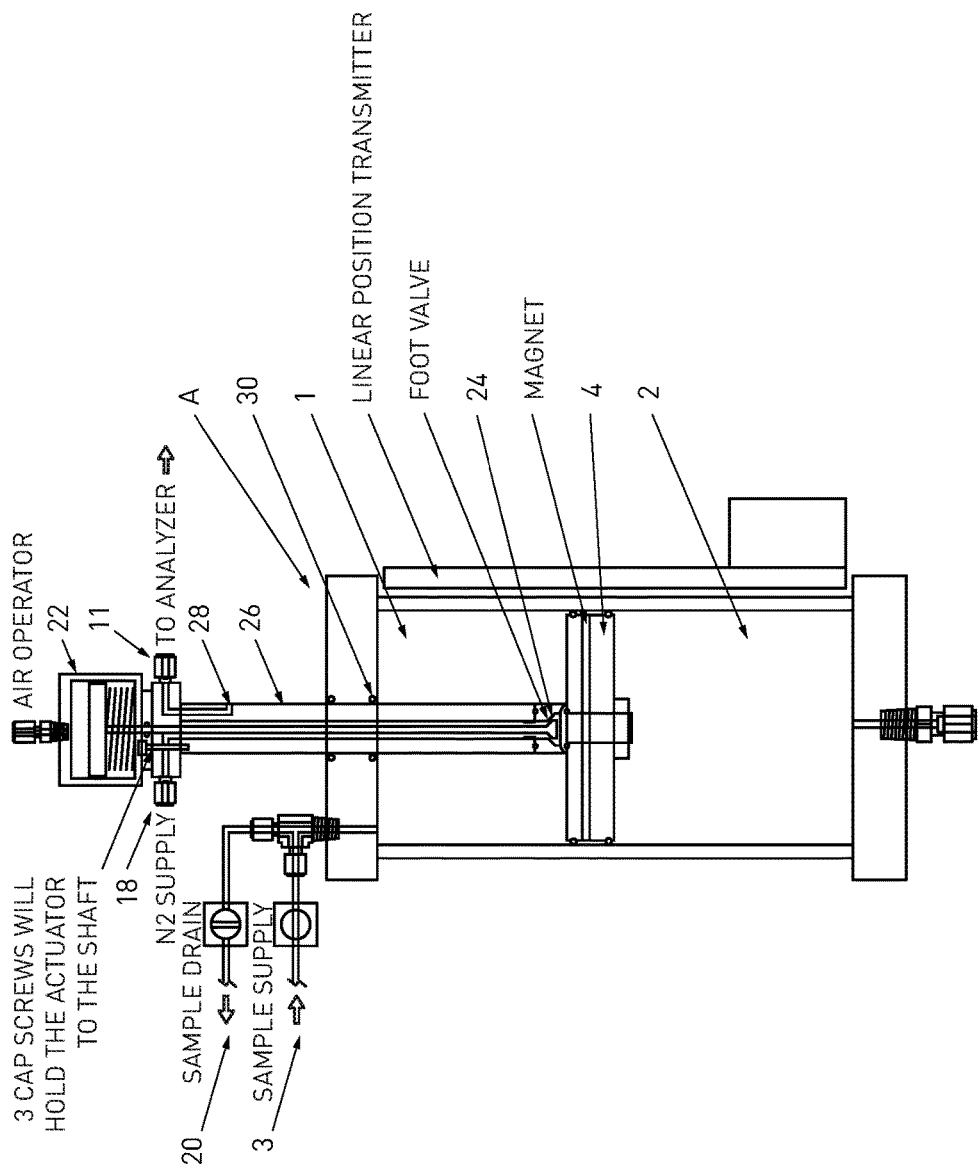
FIG. 3 is a cross-sectional side view of a first cylinder of a further embodiment of a device used to sample dirty hydrocarbons from a high pressure pipe which includes the introduction of a gaseous carrier according to the present disclosure.

Referring to FIG. 3, the apparatus is shown having a shaft 26 extending through the top plate of the first cylinder A and at its bottom end, attaching to the first piston 4. Seals are positioned around the shaft to prevent contamination of the upper portion 1 of the first cylinder A by the environment.

Disposed on the shaft 26 is a gas supply valve 18. The gas supply valve 18 is designed to allow for the introduction of a gaseous carrier gas, for example nitrogen, into the upper portion 1 of the first cylinder A and into contact with a sample of liquid hydrocarbon taken from the high pressure pipe 14. The gaseous carrier can liberate volatile components from the liquid stream into vapour phase so that they can be measured by an analyzer.

When a user wants to determine the amount of a volatile component in a liquid stream, for example $H_2S$, the following process can be used.

As discussed above, the inlet valve 3 would open and begin filling the upper portion 1 of the first cylinder A with a pressurized sample, for example a liquid hydrocarbon, from the liquid stream and move the first piston 4 downwards. In one embodiment a linear position transmitter can track the position of the first piston 4 through a magnet that is embedded in the first piston 4.

Once the first piston 4 has reached a pre-determined position, or set point, the inlet valve 3 is closed. In some cases, once the first piston 4 has reached about 30% of travel the inlet valve 3 will close. It is anticipated that the sample will be 100% liquid and at a pressure well above the bubble point for the sample.

In some cases the system can hold this state for a period to ensure that there are no valve leaks and/or seal leaks in the apparatus. This is accomplished by monitoring the position of the first piston 4. Movement greater than a limit configured in the control system can trigger an alarm and stop the execution of the process.

In some embodiments, if the first piston 4 travels past 90% of full travel there can be a safety feature in the control system that will open the sample drain valve 20 so that the first cylinder A can never be 100% filled with a sample, which would make the first cylinder A susceptible to thermal expansion pressure forces. The sample drain valve 20 can be of the "air to close" type valve with a spring that will open the valve. The inlet valve 3 can be of the "air to open" type valve with a spring that will close the valve.

As discussed above, once the sample has entered the first cylinder A, pressure can be bled off through the use of a pressure regulator 10. The specific pressure can be determined by a number of factors including the requirements of the analyzer downstream. For example, a higher pressure allows for the apparatus to take advantage of a pressure drop to eliminate liquid entrainment prior to the analyzer, but must be weighed against potentially reducing the speed at which the volatile compounds are liberated into the vapour phase. Actual pressures can range from vacuum to 100 psi.

When the pressure regulator 10 has reached its set point the actuator 22, which can be electric or pneumatic, can be activated to actuate the foot valve 24 near the bottom of the shaft 26. This allows a gas to enter the upper portion 1 of the first cylinder A, pushing the first piston 4 downwards and creating a vapour space at the top of the upper portion 1 of the first cylinder A. The downward force on the first piston 4 will continue until the shaft 26 reaches a set point within the first cylinder A. This set point may be the position where an internal passage 28 in the shaft 26 passes the inner seal 30 and allows vapour to escape the upper portion 1 of the first cylinder A. The escape of vapour from the upper portion 1 of the first cylinder A may alternatively occur via an external passage (not shown) disposed on the shaft 26.

It is preferred that the flow of gas into the upper portion 1 of the first cylinder A will be at a rate sufficient to create turbulence in the sample to liberate the analyte into the vapor phase.

The vapour, which includes the injected gas and analyte, can be conditioned in a liquid/vapour separator filter in order to control the flow and/or pressure as the vapour enters the analyzer.

It is contemplated that the analyzer can integrate the concentration of the analyte in the vapour over time, by either chemical means such as a lead acetate tape or tube or by an area under the curve method by a TDL or similar fast responding analyzer.

In some embodiments, the gas continues to purge into the upper portion 1 of the first cylinder A, until a detector, which is analyzing the analyte in the vapour, stops changing values or the concentration of the analyte drops to zero. Once the concentration of the analyte reaches zero, the entire volatile component has been removed from the sample.

The concentration of the volatile component can be referenced against previous testing to determine the concentration in the liquid hydrocarbon. For example, when using a Draeger tube style detector the measurement is essentially based on first principles, however with a continuous analyzer the system must be calibrated as a complete unit to account for errors in the flow measurement to the analyzer as well as drift in the analyzer.

Once all the analyte has been removed or the value on the detector stops changing, the gas supply valve 18 can be closes and the sample drain valve 20 can be opened to allow the remaining gas and liquid sample to be evacuated from the upper portion 1 of the first cylinder A.

Once the first piston 4 has reached a specific set point or position, for example the top of the upper portion 1 of the first cylinder A, or 0% of travel, the sample drain valve 20 can be closed. The location of the first piston 4 can be verified by a position transmitter on or within the first piston 4. At this point the apparatus is ready to start another measurement sequence.

Broadly stated, some embodiments of the present disclosure may offer certain advantages. First, by having no orifice or space through which the sample fluid must pass, there can be a reduction in the tendency of the apparatus to become plugged. Second, any leakage of the sample into other components of the apparatus downstream of the first piston 4 would simply contaminate the intermediary/hydraulic fluid, which can be changed if needed, and limit any mechanical damage to the apparatus. Thirdly, the apparatus may be safer than prior art devices because the fill rate of the first cylinder A from the high pressure pipe 14 is controlled, thereby preventing uncontrolled filling, which could damage the apparatus.

In some embodiments, by including an intermediary fluid between the two floating pistons, the system can be extremely resilient to piston seal damage that can be caused by the sample fluid for at least three reasons. First, because the pressure is typically balanced closely across the piston, there is little dynamic force driving the sample fluid and hydraulic fluid to mix. Second, because the hydraulic fluid can leave a slight film of oil on the cylinder wall, lubrication can be assured even if the sample fluid is not a particularly good lubricator. Third, even as the intermediary fluid becomes contaminated the apparatus can continue to function without fault. The hydraulic fluid, when properly selected, can be capable of suspending and binding much of the potential contamination from the sample fluid.

The apparatus is designed to handle high pressure, dirty, and viscous samples and without being susceptible to the common problems associated with sparger or membrane type devices. In some embodiments, there is no need to measure or accurately control the flow rate of the sample. The contamination on the exchange mechanism that would typically occur and cause the analysis of the sample to drift is limited or eliminated with the present apparatus. In embodiments where no filtration is required a significant maintenance requirement is eliminated. In some embodiments, shaft and piston seals can be sufficiently robust to stand up to aggressive particulate laden liquid hydrocarbon streams.

Additionally, in specific embodiments, a sight glass 16 can be included on connecting means 7 so that there is an ability to monitor the condition and quantity of the intermediary fluid. The condition of the intermediary fluid contained in the connecting means 7 can be an excellent predictor of the condition of the dynamic seals of the first piston 4. This feature can allow for the possibility of predictive maintenance, rather than requiring disassembly to inspect seals during preventative maintenance.

In some embodiments, the second piston 9 seals can be extremely reliable due to good lubrication and minimal contamination. The intermediary fluid can protect the pneumatic seals which can operate under minimal lubrication and, in the case of a hydraulically actuated application, can protect the pump from wear associated with contaminated fluid.

Seal leakage can be acceptable to the extent that the volume of fluid in the intermediary stage expands by approximately 30%. That means that up to 30% of the volume of the fluid in the intermediary fluid can be sample fluid that has leaked into the intermediary fluid. The purpose of a limit such as this is to protect the flow limiting means 8 and the secondary piston 9 seal, but can also be practically limited by the length of the second cylinder B. If the volume of the intermediary fluid is increased by more than 30%, this may not allow for the full travel of the first piston 4 and complete fill of the upper portion 1 of the first cylinder A.

In some embodiments, two magnetically coupled limit switches on the second cylinder B can monitor and notify the user if the intermediary fluid volume becomes excessive. In this case, the second piston 9 can move to a point that is close to its limit of travel, tripping the switch. More specifically, in these embodiments, by positioning the limit switches appropriately on second cylinder B and by filing the intermediary fluid to an appropriate level so that the movement of the second piston 9 does not move past the "full" level, there is no alarm. However, if the volume of the intermediary fluid were to increase past a predetermined maximum, the alarm can go off and the operator can recognize this issue and either shut down the sampling or sample on a less frequent basis until the condition is corrected.

Also, if the limit switch alarm goes off indicating excessive fluid volume between the two pistons 4 and 9, then this can also indicate that it is time to replace the seals on the first piston 4. This can be simply done by isolating the system from process pressure and then removing the first cylinder A's end cap. With a little air pressure added on top of the piston 4 it can pop out the end of the cylinder. Replacement of the seals, typically PolyPak™ designs, can be easily done with a pick tool. The piston can then be re-inserted with the use of a thin tapered collar.

In some embodiments, a continuous linear position transmitter, coupled magnetically to a magnet contained within second piston 9, can monitor the position of second piston 9 throughout the entire range of travel. By so doing, this can allow for software adjustments to be made for alarm set points and better condition monitoring as the pistons change positions relative to each other.

In some embodiments, the system can include an integrated sample recovery unit that collects spent samples and periodically sends them back to the process pipe. For example, typical for a sample system, ANSI 150 up to ANSI 1500 systems can be used. The sample recovery unit can include a diaphragm/piston type pump that has no seals to leak and can pump solids and dirty hydrocarbons without damage.

The automation of the system, in some embodiments, can be controlled by an embedded PLC program. For remote sites, the preferred embodiment can include a remote access package available via cellular connection. The system can also include an industrial and hazardous area rated touchscreen to allow for user friendly tuning and troubleshooting of the entire system.

Although a few embodiments have been shown and described, it will be appreciated by those skilled in the art that various changes and modifications might be made without departing from the scope of the invention. The terms and expressions used in the preceding specification have been used herein as terms of description and not of limitation, and there is no intention in the use of such terms and expressions of excluding equivalents of the features shown and described or portions thereof, it being recognized that the invention is defined and limited only by the claims that follow.

While the above description details certain embodiments of the invention and describes certain embodiments, no matter how detailed the above appears in text, the invention can be practiced in many ways. Details of the apparatuses and methods may vary considerably in their implementation details, while still being encompassed by the invention disclosed herein. These and other changes can be made to the invention in light of the above description.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification. Accordingly, the actual scope of the invention encompasses not only the disclosed embodiments, but also all equivalent ways of practicing or implementing the invention.

The above description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. The elements and acts of the various embodiments described above can be combined to provide further embodiments.

While certain aspects of the invention are presented below in certain claim forms, the inventors contemplate the various aspects of the invention in any number of claim forms. Accordingly, the inventors reserve the right to add additional claims after filing the application to pursue such additional claim forms for other aspects of the invention.

I claim:

1. An apparatus for sampling dirty hydrocarbons from a high pressure pipe, the apparatus comprising:
   a first cylinder having an upper and a lower portion separated by a first piston moveably disposed inside the first cylinder;
   an inlet valve for fluidly connecting the upper portion of the first cylinder with the high pressure pipe;
   an outlet valve fluidly connecting the upper portion of the first cylinder with an analyzing device;
   a second cylinder having an upper and lower portion that are separated by a second piston moveably disposed inside the second cylinder;
   a conduit fluidly connecting the lower portion of the first cylinder to the upper portion of the second cylinder; and
   a flow restrictor functionally connected to the conduit and configured for regulating fluid flow rate through the conduit.

2. The apparatus of claim 1, further comprising a pressure regulator functionally connected to the lower end of the second cylinder.

3. The apparatus of claim 2, wherein the pressure regulator is a self-regulating pressure regulator or an electronically controlled pressure regulating valve.

4. The apparatus of claim 1, further comprising a filter positioned between the high pressure pipe and the inlet valve of the first cylinder.

5. The apparatus of claim 1, further comprising a magnet embedded in the first piston.

6. The apparatus of claim 1, further comprising a magnet embedded in the second piston.

7. The apparatus of claim 1, further comprising a sight glass disposed on the conduit.

8. The apparatus of claim 1, further comprising:
   a moveable shaft extending through the top of the first cylinder and connected at its lower end to the first piston;
   a gas supply valve disposed on the shaft above the first cylinder for functionally connecting a supply of gas to the upper portion of the first cylinder;
   a foot valve positioned within the shaft to regulate to flow of gas from the gas supply valve to the upper portion of the first cylinder; and
   an actuator functional connected to the shaft in order to actuate the foot valve.

9. A method of sampling volatile components of dirty hydrocarbons from a high pressure pipe, comprising the steps of:
   providing an apparatus of claim 8;
   supplying pressurized dirty hydrocarbons from the high pressure pipe to the apparatus;
   filling the upper portion of the first cylinder with a sample of the dirty hydrocarbons;
   allowing the pressure in upper portion of the first cylinder to equalize with the pressure in the lower portion of the second cylinder;
   opening the gas supply valve;
   activating the actuator to actuate the foot valve and allow gas to flow into the upper portion of the first cylinder;
   creating a vapour in the upper portion of the first cylinder; and
   discharging a sample of vapour from the upper portion of the first cylinder to an analyzing device.

10. The method of claim 9, further comprising the step of filtering the dirty hydrocarbons prior to filling the upper portion of the first cylinder with the sample of the dirty hydrocarbons.

11. The apparatus of claim 8, wherein the outlet valve is disposed on the shaft and functionally connects the upper portion of the first cylinder with the analyzing device so that vapour in the upper portion of the first cylinder can reach the analyzing device when the shaft has reached a set point within the upper portion of the first cylinder.

12. A method of sampling dirty hydrocarbons from a high pressure pipe, comprising the steps of:
   providing an apparatus of claim 1;
   supplying pressurized dirty hydrocarbons from the high pressure pipe to the apparatus;
   filling the upper portion of the first cylinder with a sample of the dirty hydrocarbons;
   allowing the pressure in upper portion of the first cylinder to equalize with the pressure in the lower portion of the second cylinder; and
   discharging the sample of dirty hydrocarbon from the upper portion of the first cylinder under pressure to an analyzing device.

13. The method of claim 12, further comprising the step of filtering the dirty hydrocarbons prior to filling the upper portion of the first cylinder with the sample of the dirty hydrocarbons.

* * * * *